United States Patent [19]

Kagiya et al.

[11] Patent Number: 4,820,844

[45] Date of Patent: Apr. 11, 1989

[54] RADIATION SENSITIZER

[75] Inventors: Tsutomu Kagiya, Kyoto; Motonobu Minagawa, Koshigaya; Yutaka Nakahara, Iwatsuki; Ryoji Kimura, Kyoto; Tsuneo Tsubakimoto, Toyonaka; Ryoichi Oshiumi, Ibaraki; Koichi Sakano, Kyoto, all of Japan

[73] Assignees: Adeka Argus Chemical Co., Ltd., Tokyo; Kyoto University, Kyoto, both of Japan

[21] Appl. No.: 896,135

[22] Filed: Aug. 12, 1986

[30] Foreign Application Priority Data

Aug. 15, 1985 [JP] Japan .................................. 60-178549
Dec. 12, 1985 [JP] Japan .................................. 60-277975

[51] Int. Cl.$^4$ .......................................... C07D 249/08
[52] U.S. Cl. ..................................... 548/266; 544/132; 544/366; 548/255; 546/210; 536/22; 536/23
[58] Field of Search ......................... 548/266, 338, 339

[56] References Cited

U.S. PATENT DOCUMENTS 4,371,540 2/1983 Lee et al. ............................ 548/338
4,462,992 7/1984 Agrawal et al. ...................... 548/33

OTHER PUBLICATIONS

Magden, 94:214629b, Agent for Radiation-Sensitizing Tumor Cells.
Sehgal et al., 94:174982c, Potential Ratio Sensitizing Agents.
Stanley et al., 89:191009e, Influence of Tumor Size on Radiosensitization by Misonidazole.
Asquith et al., 82:92970k.
Kofman et al I., 97:182306n.
Kofman et al II., 88:22771w.
Terpigorev et al I., 96:181213x.
Terpigorev et al II., 97:6096k.
Ostapkovich et al., 91:15766y.

*Primary Examiner*—Glennon H. Hollrah
*Assistant Examiner*—Peter G. O'Sullivan
*Attorney, Agent, or Firm*—Frishauf, Holtz, Goodman & Woodward

[57] ABSTRACT

A radiation sensitizer of the present invention contains a particular nitrotriazole compound as an active ingredient and accelerates inactivation of intractable hypoxic cells in a malignant tumor by irradiation.

2 Claims, No Drawings

RADIATION SENSITIZER

FIELD OF THE INVENTION

This invention relates to a radiation sensitizer. More particularly, it relates to a radiation sensitizer which contains a particular nitrotriazole compound as an active ingredient and accelerates inactivation of intractable hypoxic cells in a malignant tumor by irradiation.

DESCTIPTION OF PRIOR ARTS

Conventional therapeutics for malignant tumors include radiotherapy, surgical treatments, chemotherapy and immunotherapy. In particular, radiotherapy is highly effective and has been employed for a long time.

However there are still some problems in that the radiotherapy can not always give complete recovery and that relapse of apparently cured tumor is sometimes observed.

These problems are caused by the fact that a tumor tissue per se has more or less radiation resistance and that some radiation-resistant oxygen-deficient cells are present in a tumor. In fact, the result of an irradiation test indicates that cells in an atomsphere free from oxygen have a radiation resistance two or three times as high as that of cells present together with oxygen.

Therefore it has been urgently required to develop a sensitizer for hypoxic cells which elevate the sensitivity of the hypoxic cells to radiation in order to remarkably enhance the radiotherapeutic effect.

From this point of view, there have been developed some sensitizers for hypoxic cells. Nitroimidazole derivatives are well known examples thereof.

Misonidazole, which is a typical nitroimidazole derivative, exhibits a sensitizing effect approximately twice as high as that observed in the absence of the same in a tumor transplantation test with animals. However the neurotoxicity thereof makes it difficult to administer a large amount of this compound. Thus no sensitizing effect is observed when it is administered to human subjects in a clinically acceptable dose.

SUMMARY OF THE INVENTION

Under these circumstances, we have attempted to find out a compound which has a low toxicity as well as a higher sensitizing effect and have found that nitrotriazole compound having particular substituents as shown by the following general formulas (I), (II), (III) and (IV) remarkably elevate the sensitivity of hypoxic cells to radiation to thereby enhance the radiotherapeutic effect.

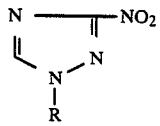
(I)

(wherein R is

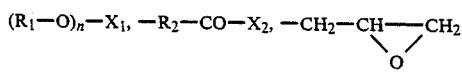

or a residue of sugar, $R_1$ is alkylene, $X_1$ is hydrogen or acyl, n is an integar from 1 to 5, $R_2$ is alkylene, hydroxyalkylene or arylene, $X_2$ is $-O-R_3$ or $-N(R_4)R_5$, $X_3$ is halogen, acyloxy, $-O-R_3$ or $-N(R_4)R_5$, $R_3$ is hydrogen, alkyl, hydroxyalkyl, alkyl containing ether linkage in the molecule or a residue of sugar, $R_4$ is hydrogen, alkyl, hydroxyalkyl, alkyl containing ether linkage in the molecule or alkyl containing ether linkage and hydroxyl in the molecule, $R_5$ is a group represented by $R_5$ or $-R_6-N(R_7)R_8$, $R_6$ is alkylene, $R_7$ and $R_8$ each is a group represented by $R_5$, $R_4$ and $R_5$ or $R_7$ and $R_8$ may be connected to form alkylene or exadialkylene, and $R_4$ and $R_7$ may be connected to form alkylene.)

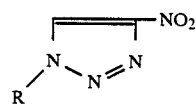
(II)

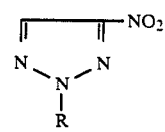
(III)

(wherein R is

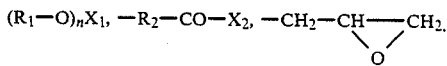

or a residue of sugar, $R_1$ is alkylene, alkenylene or alkynylene, $X_1$ is hydrogen, alkyl or acyl, n is an integar from 1 to 5, $R_2$ is alkylene, hydroxyalkylene or arylene, $X_2$ is $-O-R_3$ or $-N(R_4)R_5$, $X_3$ is halogen, acyloxy, $-0-R_3$ or $-N(R_4)R_5$, $R_3$ is hydrogen, alkyl, hydroxyalkyl, alkyl containing ether linkage in the molecule, alkyl containing ether linkage and hydroxyl in the molecule or a residue of sugar, $R_4$ is hydrogen, alkyl, hydroxyalkyl, alkyl containing ether linkage in the molecule or alkyl containing ether linkage and hydroxyl in the molecule, $R_5$ is a group represented by $R_5$ or $-R_6-N(R_7)R_8$, $R_6$ is alkylene, $R_7$ and $R_8$ each is a group represented by $R_5$, $R_4$ and $R_5$ or $R_7$ and $R_8$ may be connected to form alkylene or oxadialkylene, and $R_4$ and $R_7$ may be connected to form alkylene.)

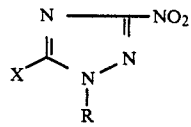
(IV)

(wherein X is halogen or $-CO-R_1$, $R_1$ is $-O-R_2$ or $-N(R_3)R_4$, $R_2$ and $R_3$ each is hydrogen, alkyl, hydroxyalkyl, alkyl containing ether linkage in the molecule or alkyl containing ether linkage and hydroxyl in the molecule, $R_4$ is a group represented by $R_3$ or $-R_5-N(R_6)R_7$, $R_5$ is alkylene, $R_6$ and $R_7$ each is a group represented by $R_3$, $R_3$ and $R_4$ or $R_6$ and $R_7$ may be connected to form alkylene or oxadialkylene, and $R_3$ and $R_6$ may be connected to form alkylene, R is hydrogen, alkyl, hydroxyalkyl, $-CH_2-CH-CH_2$, $-CH_2-CH(OH)-CH_2-Y$ or
  \\  /
   O -continued $$-R_8-CO-R_1,$$

$R_8$ is alkylene, Y is halogen, acyloxy, $-O-R_2$ or $-N(R_3)R_4$.)

Based on this finding, we have completed the present invention.

Accordingly, the present invention provides a radiation sensitizer containing a nitrotriazole compound represented by the above general formura (I), (II), (III) or (IV) as an active ingredient.

DESCRIPTION OF THE PREFERRED EMBODIMENTS

In the nitrotriazole compound represented by the general formula (I), it is preferable that R is $-R_2-CO-X_2$ or $-CH_2-CH(OH)-CH_2-X_3$, and further, $R_2$ is alkylene, $X_2$ is $-N(R_4)R_5$, and $X_3$ is halogen.

In the nitrotriazole compound represented by the general formula (II) and (III), it is preferable that R is $-R_2-CO-X_2$ or $-CH_2-CH(OH)-CH_2-X_3$, and further, $R_2$ is alkylene, $X_2$ is $-N(R_4)R_5$, and $X_3$ is halogen.

In the nitrotriazole compound represented by the general formula (IV), it is preferable that R is $-R_8-CO-R_1$ or $-CH_2-CH(OH)-CH_2-Y$, and further, $R_8$ is alkylene, $R_1$ is $-N(R_4)R_5$, and Y is halogen.

In the compounds represented by the above general formulas (I), (II), (III) and (IV), alkyl includes methyl, ethyl, propyl, isoproply, butyl, isobutyl, sec-butyl, amyl, hexyl, heptyl, octyl, isooctyl and 2-ethylhexyl; hydroxyalkyl includes 2-hydroxyethyl and 2-hydroxypropyl; alkyl containing ether linkage in the molecule includes methoxyethyl, ethoxyethyl, butoxyethyl and ethoxyethoxyethyl; alkyl containing ether linkage and hydroxyl in the molecule includes 2-(2′-hydroxyethoxy)ethyl; alkylene includes methylene, ethylene, trimethylene, 1,2-propylene, tetramethylene, pentamethylene, 1,5-hexylene, 2,6-heptylene, and hexamethylene; oxadialkylene includes oxadialkylene; arylene includes phenylene; acyl includes acetyl, propionyl, acryloyl, methacryloyl, benzoyl and toluoyl; residue of sugar includes a residue of arabinose, ribose, xylose, fractose, galactose, glucose, mannose, sorbose, glucoheptose, lactose, maltose, sucrose, trehalose, melezitose, raffinose, dextrin, cyclodextrin and glycogen.

The typical examples of the compounds represented by the above general formula (I) are as follows:
2-(3′-nitro-1-triazolyl) acetic acid,
2-(3′-nitro-1′-triazolyl) acetic acid methyl ester,
2-(3′-nitro-1′-triazolyl) acetic acid ethyl ester,
2-(3′-nitro-1′-triazolyl) acetic acid hydroxyethyl ester,
2-(3′-nitro-1′-triazolyl) acetic acid ethoxyethyl ester,
2-(3′-nitro-1′-triazolyl) acetic acid hydroxyetyhoxyethyl ester,
2-(3′-nitro-1′-triazolyl) acetic acid glucose ester,
2-(3′-nitro-1′-triazolyl) acetic acid morpholide,
2-(3′-nitro-1′-triazolyl) acetic acid diethylamide,
2-(3′-nitro-1′-triazolyl) acetic acid butylamide,
2-(3′-nitro-1′-triazolyl) acetoamide,
2-(3′-nitro-1′-triazolyl) acetic acid-3″-dimethylaminopropylamide,
2-(3′-nitro-1′-triazolyl) acetic acid diethanolamide,
2-(3′-nitro-1′-triazolyl) acetic acid ethanolamide,
2-(3′-nitro-1′-triazolyl) acetic acid isopropanolamide,
2-(3′-nitro-1′-triazolyl) acetic acid propanolamide,
2-(3′-nitro-1′-triazolyl) acetic acid-2″-methoxyethylamide,
2-(3′-nitro-1′-triazolyl) acetic acid-2″-morpholinoethylamide,
2-(3′-nitro-1′-triazolyl) acetic acid piperidide,
2-(3′-nitro-1′-triazolyl) acetic acid-4″-methylpiperadide,
3-(3′-nitro-1′-triazolyl) propionic acid methyl ester,
3-(3′-nitro-1′-triazolyl) propionic acid ethanolamide,
3-(3′-nitro-1′-triazolyl) propionic acid dimethylamide,
3-(3′-nitro-1′-triazolyl) propionic acid ethylamide,
3-(3′-nitro-1′-triazolyl) propionic acid morpholide,
3-(3′-nitro-1′-triazolyl) propionic acid-2″-piperidinoethylamide,
3-(3′-nitro-1′-triazolyl) propionic acid-3″-morpholinopropylamide,
3-(3′-nitro-1′-triazolyl) propionic acid lactic acid methyl ester,
1-(2′,3′-epoxypropyl)-3-nitrotriazole,
1-(2′,3′-dihydroxypropyl)-3-nitro-triazole,
1-(2′-hydroxy-3′-methoxypropyl)-3-nitro-triazole,
1-(2′-hydroxy-3′-ethoxypropyl)-3-nitro-triazole,
1-(2′-hydroxy-3′-chloropropyl)-3-nitro-triazole,
1-(2′-hydroxy-3′-dimethylaminopropyl)-3-nitrotriazole,
1-(2′-hydroxy-3′-piperidinopropyl)-3-nitrotriazole,
1-(2′-hydroxy-3′-morpholinopropyl)-3-nitrotriazole,
1-[2′-hydroxy-3′-(3″-dimethylaminopropylaminopropyl)]-3-nitrotriazole,
1-(2′-hydroxy-3′-acetyloxypropyl)-3-nitrotriazole,
1-(2′-oxo-3′-methoxy-propyl)-3-nitrotriazole),
1-(2′-oxo-3′-butylaminopropyl)-3-nitrotriazole,
1-(2′-hydroxyethyl)-3-nitrotriazole,
1-(2′-hydroxypropyl)-3-nitrotriazole,
1-(hydroxymethyl)-3-nitrotriazole,
1-(2′-acetyloxyethyl)-3-nitrotriazole,
1-(hydroxyethoxyethyl)-3-nitrotriazole,
1-(2′-hydroxy-3′-N-azilidinopropyl)-3-nitrotriazole,
1-(3′-nitro-1′-triazolyl)glucose,
1-(3′-nitro-1′-triazolyl)ribose,
1-(3′-nitro-1′-triazolyl)maltose, etc.

These compounds may be an acid addition salt thereof, and the acid includes inorganic acid such as hydrochloric acid, hydrobromic acid, sulfuric acid, nitric acid and phosphoric acid and organic acid such as acetic acid, propionic acid, oxalic acid, citric acid, tartaric acid, adipic acid, lactic acid and p-toluene sulfonic acid.

Some of these compounds are known and some of them are novel, and novel compounds can be prepared by reacting 3-nitro-1,2,4-triazole with halocarboxylic acid esters or unsaturated carboxylic acid esters followed by hydrolyzing, ester exchanging or reacting with amines if necessary; reacting 3-nitro-1,2,4-triazole with epihalohydrines followed by reacting with carboxylic acids, amines or alcohols if necessary; reacting 3-nitro-1,2,4-triazole with alkylene oxides followed by acylation if necessary; reacting 3-nitro-1,2,4-triazole with sugars.

The typical examples of the compounds represented by the above general formulas (II) and (III) are as follows:
2-(4′-nitro-1′-triazolyl) acetic acid,
2-(4′-nitro-1′-triazolyl) acetic acid methyl ester,
2-(4′-nitro-2′-triazolyl) acetic acid methyl ester,
2-(4′-nitro-1′-triazolyl) acetic acid ethyl ester, 2-(4'-nitro-1'-triazolyl) acetic acid hydroxyethyl ester,
2-(4'-nitro-1'-triazolyl) acetic acid ethoxyethyl ester,
2-(4'-nitro-1'-triazolyl) acetic acid hydroxyethoxyethyl ester,
2-(4'-nitro-1'-triazolyl) acetic acid glucose ester,
2-(4'-nitro-1'-triazolyl) acetoamide,
2-(4'-nitro-2'-triazolyl) acetoamide,
2-(4'-nitro-1'-triazolyl) acetic acid morpholide,
2-(4'-nitro-1'-triazolyl) acetic acid diethylamide,
2-(4'-nitro-1'-triazolyl) acetic acid butylamide,
2-(4'-nitro-1'-triazolyl) acetic acid-3''-dimethylaminopropylamide,
2-(4'-nitro-1'-triazolyl) acetic acid diethanolamide,
2-(4'-nitro-1'-triazolyl) acetic acid ethanolamide,
2-(4'-nitro-2'-triazolyl) acetic acid ethanolamide,
2-(4'-nitro-1'-triazolyl) acetic acid propanolamide,
2-(4'-nitro-2'-triazolyl) acetic acid propanolamide,
2-(4'-nitro-1'-triazolyl) acetic acid-2''-methoxyethylamide,
2-(4'-nitro-2'-triazolyl) acetic acid-2''-methoxyethylamide,
2-(4'-nitro-1'-triazolyl) acetic acid-2''-merpholinoethylamide,
2-(4'-nitro-1'-triazolyl) acetic acid piperidide,
2-(4'-nitro-1'-triazolyl) acetic acid-4''-methylpiperadide,
3-(4'-nitro-1'-triazolyl) propionic acid methyl ester,
3-(4'-nitro-1'-triazolyl) propionic acid ethanolamide,
3-(4'-nitro-1'-triazolyl) propionic acid dimethylamide,
3-(4'-nitro-1'-triazolyl) propionic acid ethylamide,
3-(4'-nitro-1'-triazolyl) propionic acid morpholide,
3-(4'-nitro-1'-triazolyl) propionic acid-2''-piperidinoethylamide,
3-(4'-nitro-1'-triazolyl) propionic acid-3''-morpholinopropylamide,
3-(4'-nitro-1'-triazolyl) lactic acid methyl ester,
1-(2',3'-epoxypropyl)-4-nitrotriazole,
2-(2'3'-epoxypropyl)-4-nitrotriazole,
1-(2',3'-dihydroxypropyl)-4-nitrotriazole,
1-(2'-hydroxy-3'-methoxypropyl)-4-nitrotriazole,
2-(2'-hydroxy-3'-methoxypropyl)-4-nitrotriazole,
1-(2'-hydroxy-3'-ethoxypropyl)-4-nitrotriazole,
1-(2'-hydroxy-3'-chloropropyl)-4-nitrotriazole,
2-(2'-hydroxy-3'-chloropropyl)-4-nitrotriazole,
1-(2'-hydroxy-3'-dimethylaminopropyl)-4-nitrotriazole,
1-(2'-hydroxy-3'-piperidinopropyl)-4-nitrotriazole,
2-(2'-hydroxy-3'-piperidinopropyl)-4-nitrotriazole,
1-(2'-hydroxy-3'-morpholinopropyl)-4-nitrotriazole,
2-(2'-hydroxy-3'-morpholinopropyl)-4-nitrotriazole,
1-(2'-hydroxy-3'-aziridinopropyl)-4-nitrotriazole,
2-(2'-hydroxy-3'-aziridinopropyl)-4-nitrotriazole,
1-[2'-hydroxy-3'-(3''-dimethylaminopropylaminopropyl)]-4-nitrotiazole,
1-(2'-hydroxy-3'-acetyloxypropyl)-4-nitrotriazole,
1-(2'-oxo-3'-methoxypropyl)-4-nitrotriazole,
1-(2'-oxo-3'-butylaminopropyl)-4-nitrotriazole,
1-(2'-hydroxyethyl)-4-nitrotirazole,
1-(2'-hydroxypropyl)-4-nitrotriazole,
1-(hydroxymethyl)-4-nitrotriazole,
1-(2'-acetyloxy-ethyl)-4-nitrotriazole,
1-(hydroxyethoxyethyl)-4-nitrotriazole,
1-(4'-methoxy-2-butynyl)-4-nitro-triazole,
1-(4'-nitro-1'-triazolyl) glucose,
1-(4-nitro-1-triazolyl) ribose,
1-(4'-nitro-1'-triazolyl) ribofuranose,
2-(4'-nitro-1'-triazolyl) ribofuranose,
1-(4'-nitro-1'-triazolyl) maltose, etc.

These compounds may be an acid addition salt thereof, and the acid includes inorganic acid such as hydrochloric acid, hydrobromic acid, sulfuric acid, nitric acid and phosphoric acid and organic acid such as acetic acid, propionic acid, oxalic acid, citric acid, tartaric acid, adipic acid, lactic acid and p-toluene sulfonic acid.

Some of these compounds are known and some of them are novel, and novel compounds can be prepared by reacting 4-nitro-1,2,3-triazole with halocarboxylic acid esters or unsaturated carboxylic acid esters followed by hydrolyzing, ester exchanging or reacting with amines if necessary; reacting 3-nitro-1,2,4-triazole with epihalohydrines follwed by reacting with carboxylic acids, amines or alcohols if necessary; reacting 3-nitro-1,2,4-triazole with alkylene oxides followed by acylation if necessary; reacting 3-nitro-1,2,4-triazole with sugars.

The typical examples of the compounds represented by the above general formula (IV) are as follows:

2-(3'-nitro-5'-bromo-1',2',4'-triazole-1'-yl) acetic acid ethanolamide,
2-(3'-nitro-5'-bromo-1',2',4'-triazole-1'-yl) acetic acid diethanolamide,
2-(3'-nitro-5'-bromo-1',2',4'-triazole-1'-yl) acetic acid methoxyethylamide,
1-(3'-methoxy-2'-hydroxypropyl)-3-nitro-5-bromo-1,2,4-triazole,
1-methyl-3-nitro-1,2,4-triazole-5-carboxylic acid methyl ester,
3-nitro-1,2,4-triazole-5-carboxylic acid methoxyethylamide,
1-methoxycarbonylmethyl-3-nitro-1,2,4-triazole-5-carboxylic acid methyl ester,
1-(3'-methoxy-2'-hydroxypropyl)-3-nitro-1,2,4-triazole-5-carboxylic acid methyl ester,
1-methyl-3-nitro-1,2,4-triazole-5-carboxylic acid ethanolamide,
1-(2',3'-epoxypropyl)-3-nitro-1,2,4-triazole-5-carboxylic acid ethanolamide,
1-(3'-methoxy-2'-hydroxypropyl)-3-nitro-1,2,4-triazole-5-carboxylic acid ethanolamide,
1-(3'-acetoxy-2'-hydroxypropyl)-3-nitro-1,2,4-triazole-5-carboxylic acid ethanolamide,
1-(2'-hydroxyethyl)-3-nitro-1,2,4-triazole-5-carboxylic acid ethanolamide,
1-(2'-hydroxyethylcarbamoylmethyl)-3-nitro-1,2,4-triazole-5-carboxylic acid ethanolamide,
3-nitro-1,2,4-triazole-5-carboxylic acid methoxyethylamide,
1-methoxycarbonyl-methyl-3-nitro-1,2,4-triazole-5-carboxylic acid methoxyethylamide,
1-(2'-hydroxyethylcarbamoylmethyl)-3-nitro-1,2,4-triazole-5-carboxylic acid methoxyethylamide,
1-[N,N-bis(2-hydroxyethyl)carbamoylmethyl]-3-nitro-1,2,4-triazole-5-carboxylic acid methoxyethylamide,
1-(3'-aziridino-2'-hydroxypropyl)-3-nitro-1,2,4-triazole-5-carboxylic acid methoxyethylamide,
1-(2'-hydroxyethyl-carbamoylethyl)-3-nitro-1,2,4-triazole-5-carboxylic acid methoxyethylamide,
1-(hydroxyethoxycarbonyl-methyl)-3-nitro-1,2,4-triazole-5-carboxylic acid methoxyethylamide,
1-(ethoxyethoxycarbonylmethyl)-3-nitro-1,2,4-triazole-5-carboxylic acid methoxyethylamide, 1-(hydroxyethoxyethoxycarbonylmethyl)-3-nitro-1,2,4-triazole-5-carboxylic acid methoxyethylamide, 1-methyl-3-nitro-1,2,4-triazole-5-carboxylic acid diethanolamide, 1-methyl-3-nitro-1,2,4-triazole-5-carboxylic acid-2',3'-dihydroxypropylamide, 1-(morpholinocarbonylmethyl)-3-nitro-1,2,4-triazole-5-carboxylic acid morpholide, 1-(aziridinocarbonyl-methyl)-3-nitro-1,2,4-triazole-5-carboxylic acid aziridide, 1-(piperidinocarbonylmethyl)-3-nitro-1,2,4-triazole-5-carboxylic acid piperidide, 1-(4'-methoxypiperadinocarbonylmethyl)-3-nitro-1,2,4-triazole-5-carboxylic acid-(4''-methylpiperadide), 1-(diethylcarbamoylmethyl)-3-nitro-1,2,4-triazole-5-carboxylic acid diethylamide, 1-(dimethylaminopropyl-carbamoylmethyl)-3-nitro-1,2,4-triazole-5-carboxylic acid dimethylaminopropylamide, 1-(morpholinopropyl-carbamoylmethyl)-3-nitro-1,2,4-triazole-5-carboxylic acid morpholinopropylamide, etc.

These compounds may be an acid addition salt thereof, and the acid includes inorganic acid such as hydrochloric acid, hydrobromic acid, sulfuric acid, nitric acid and phosphoric acid and organic acid such as acetic acid, propionic aicd, oxalic acid, citric acid, tartaric acid, adipic acid, lactic acid and p-toluene sulfonic acid.

These compounds can be prepared by reacting 3-nitro-5-substituted-1,2,4-triazole with halocarboxylic acid esters or unsaturated carboxylic acid esters followed by hydrolyzing, ester exchanging or reacting with amines if necessary; reacting 3-nitro-5-substituted-1,2,4-triazole with epihalohydrines followed by reacting with carboxylic acids, amines or alcohols if necessary; reacting 3-nitro-5-substituted-1,2,4-triazole with alkylene oxides followed by acylation if necessary.

The following preparation examples illustrate the preparation of the compounds represented by the above general formulas (I), (II), (III) and (IV). The preparation examples 1-16 illustrate the preparation of the compounds represented by the general formula (I). The preparation examples 17-27 illustrate the preparation of the compounds represented by the general formulas (II) and (III). The preparation examples 28-39 illustrate the preparation of the compounds represented by the general formula (IV).

PREPARATION EXAMPLE 1

2-(3'-nitro-1'-triazolyl) acetic acid morpholide 2-(3'-nitro-1'-triazolyl) acetic acid methyl ester (1 g) is added to 2 ml of morpholine, and warmed at 80°-90° C. for 5 hr with stirring. The reaction mixture is evaporated and the residue recrystallized from chloroform.

Yield, 800 mg, Colorless crystals, mp 157.5°-157° C.;

IR (KBr) 3170, 1670, 1550, 1510, 1320, 1120 cm$^{-1}$;

Anal. Calcd. for $C_8H_{11}N_5O_4$: C, 39.83; H, 4.56; N, 29.05 Found: C, 39.45; H, 4.52; N, 29.00

PREPARATION EXAMPLE 2

2-(3'-nitro-1'-triazolyl) acetic acid piperadide 2-(3'-nitro-1'-triazolyl) acetic acid methyl ester (1 g) is added to 2 ml of piperidine, and warmed at 80°-90° C. for 5 hr with stirring. The excess piperidine is then removed and the residue recrystallized from chloroform.

Yield, 750 mg, Colorless crystals, mp 122.51°-123.4° C.;

IR (KBr) 3070, 1670, 1560, 1510, 1320, 1310 cm$^{-1}$;

Anal. Calcd. for $C_9H_{13}N_5O_3$: C, 45.19; H, 5.44; N, 29.29 Found: C, 44.88; H, 5.39; N, 29.33

PREPARATION EXAMPLE 3

2-(3'-nitro-1'-triazolyl) acetoamide

To a stirred suspension of 1 g of 2-(3'-nitro-1'-triazolyl) acetic acid methyl ester in 2 ml of methanol is added 2 g of 28% aqueous ammonia solution at 0°-5° C., and then stirred for 2 hr at 0°-10° C.

After standing for 1 day, a white solid is separated from the solution by filtration, and recrystallized from chloroform-methanol.mp 191°-192° C.;

IR(KBr) 3450, 3350, 3150, 1690, 1600, 1550, 1510. 1320, 1310 cm$^{-1}$;

Anal. Calcd. for $C_4H_5N_5O_3$: C, 28.07; H, 2.92; N, 40.94 Found: C, 28.25; H, 2.96; N, 40.61

PREPARATION EXAMPLE 4

2-(3'-nitro-1'-triazolyl) acetic acid ethanolamide

To a 1 g of 2-(3'-nitro-1'-triazolyl) acetic acid methyl ester in 10 ml of dioxane is added 1 g of monoethanolamine. The solution is stirred at 80°-100° C. for 1 hr.

After the solvent is removed, 10 ml of methanol is added followed by addition of 3 g of ion exchang resin (Dowex 50W).

The resin is filtered off the filtrate is evaporated.

The residue is recrystarized from methanol-ethyl acetate.

Yield 650 mg, Colorless crystals, mp 111.7°-113° C.;

IR(KBr) 3400, 3300, 1665, 1560, 1525, 1315, 1050 cm$^{-1}$;

Anal. Calcd. for $C_6H_9N_5O_4$; C, 33.49; H, 4.19; N, 32.56 Found: C, 33.46; H, 4.16; N, 32.49

PREPARATION EXAMPLE 5

2-(3'-nitro-1'-triazolyl) acetic acid butylamide

This compound is obtained in a similar manner as preparation example 4 except for the use of butylamine instead of ethanolamine. Colorless crystals, mp 89°-91° C.;

IR(KBr) 3300, 3150, 1670, 1550, 1510, 1320, 1310 cm$^{-1}$;

Anal. Calcd. for $C_8H_{13}N_5O_3$: C, 42.29; H, 5.73; N, 30.84 Found: C, 42.05; H, 5.68; N, 30.81

PREPARATION EXAMPLE 6

2-(3'-nitro-1'-triazolyl) acetic acid-2''-methoxyethylamide

This compound is obtained in a similar manner as preparation example 4 except for the use of 2-methoxyethylamine instead of ethanolamine.

Colorless crystals, mp 122.9°-123.5° C.;

IR(KBr) 3400, 3100, 1670, 1560, 1510, 1210 cm$^{-1}$;

Anal. Calcd. for $C_7H_{11}N_5O_4$; C, 36.68; H, 4.80; N, 30.57 Found: C, 36.52; H, 4.77; N, 30.45

PREPARATION EXAMPLE 7

3-(3'-nitro-1'-triazolyl) propionic acid methyl ester

A mixture of 3-nitro-1,2,4-triazole (5 g), methanol (50 ml), methyl acrylate (6 g) and triethylamine (5 ml) is refluxed for 12 hr with stirring.

The solvent and excess methyl acrylate are removed, and the residue is dissolved in chloroform, washed with dilute NaHCO₃ solution. After drying with anhyd. MgSO₄, the solvent is removed and the residue recrystallized from chloroform. Colorless crystals, mp 76.0°–76.6° C.;
IR(KBr) 3100, 1730, 1560, 1555, 1500, 1315, 1220 cm$^{-1}$;
Anal. Calcd. for $C_6H_8N_4O_4$: C, 36.00; H, 4.00; N, 28.00 Found: C, 35.85; H, 3.97; N, 28.17

PREPARATION EXAMPLE 8

3-(3'-nitro-1'-triazolyl) propionic acid ethanolamide

To a 1 g of 3-(3'-nitro-1'-triazolyl) propionic acid methyl ester in 10 ml of dioxane is added 1 g of monoethanolamine. The mixture is warmed at 90°–100° C. for 1 hr with stirring. After the solvent is removed, 10 ml of methanol is added followed by addition of 3 g of ion exchange resin (Dowex 50W).

The resin is filtered off and the filtrate is evaporated. The residue is recrystallized from methanol-ethyl acetate.

Yield 600 mg, Colorless crystals, mp 111°–112° C.;
IR(KBr) 3450, 3350, 1660, 1570, 1510, 1320, 1060 cm$^{-1}$;
Anal. Calcd. for $C_7H_{11}N_5O_4$: C, 36.68; H, 4.80; N, 30.57 Found: C, 36.66; H, 4.78; N, 30.50

PREPARATION EXAMPLE 9

3-(3'-nitro-1'-triazolyl) propionic acid morpholide

A mixture of 1 g of 3-nitro-1,2,4-triazole, 20 ml of methanol, acrylic acid morpholide (1.41 g), and 0.55 ml of 28%-NaOMe is refluxed for 12 hr with stirring.

The solvent is evaporated and the residue extracted with toluene.

After drying with anhyd.MgSO₄, the solvent is evaporated and the residue recrystallized from xylene.

Colorless crystals, mp 115°–116° C.;
IR(KBr) 3100, 1650, 1550, 1505, 1310, 1120 cm$^{-1}$;
Anal. Calcd. for $C_9H_{13}N_5O_4$: C, 42.35; H, 5.10; N, 27.45 Found: C, 42.66; H, 5.14; N, 27.08

PREPARATION EXAMPLE 10

1'-(2'-hydroxy-37-chloropropyl)-3-nitrotriazole

A mixture of 3.4 g of 3-nitro-1,2,4-triazole, 15 g of epichlorohydrin, and 0.6 g of anhyd. K₂CO₃ is warmed at 100° C. for 20 min. with stirring.

The solid is filtered off and washed with ethanol.

The combined filtrates are evaporated, and the residue is purified by chromatography on silica-gell elution with chloroform-ethanol.

Yield 5.8 g, Pale yellow liquid;
IR(neat) 3350, 3100, 1560, 1510, 1310, 1040 cm$^{-1}$;
Anal. Calcd. for $C_5H_7N_4O_3Cl$: C, 29.06; H, 3.39; N, 27.12 Found: C, 29.15; H, 3.41; N, 26.91

PREPARATION EXAMPLE 11

1-(2',3'-epoxypropyl)-3-nitrotriazole

A mixture of 5.8 g of 1-(2'-hydroxy-3'-chloropropyl)-3-nitrotriazole and 50 ml of 10% sodium hydroxide solution is stirred for 15 min. at room temperature.

The reaction mixture is extracted with chloroform (50 ml×3). The chloroform solution is treated with activated charcoal for 30 min. at 60° C. with stirring. The solid is filtered off and the filtrate is evaporated to dryness.

Yield 4.3 g, Colorless liquid;
IR(neat) 3100, 1560, 1510, 1310, 1260, 1130 cm$^{-1}$;
Anal. Calcd. for $C_5H_6N_4O_3$: C, 35.29; H, 3.53; N, 32.94 Found: C, 35.05; H, 3.52; N, 32.71

PREPARATION EXAMPLE 12

1-(2'-hydroxy-3'-methoxypropyl)-3-nitrotriazole

A mixture of 1 g of 1-(2',3'-epoxypropyl)-3-nitrotriazole, 20 ml of methanol and 2 ml of boron trifluride etherate is refluxed for 2 hr with stirring. The solvent is evaporated, and the residue is purified by chromatography on silica gel (elution with chloroform-ethanol).

Recrystallization from chloroform-hexane give colorless crystals (0.8 g). mp 67°–69.5° C.;
IR(KBr) 3300, 3100, 1560, 1510, 1310, 1110–1080 cm$^{-1}$;
Anal. Calcd. for $C_6H_{10}N_4O_4$: C, 35.64; H, 4.95; N, 27.72 Found: C, 35.63; H, 4.90; N, 27.90

PREPARATION EXAMPLE 13

1-(2'-hydroxy-3'-ethoxypropyl)-3-nitrotriazole

This compound is obtained in a simmilar manner as preparation example 12, except for using ethanol instead of methanol.

Colorless liquid;
IR(neat) 3400, 3100, 1560, 1510, 1310, 1140–1060 cm$^{-1}$;
Anal. Calcd. for $C_7H_{12}N_4O_4$: C, 38.89; H, 5.56; N, 25.93 Found: C, 38.77; H, 5.52; N, 26.15

PREPARATION EXAMPLE 14

1-(2'-hydroxy-3'-piperidinopropyl)-3-nitrotriazole

A mixture of 1 g of 1-(2',3'-epoxypropyl)-3-nitrotriazole, 4 g of piperidine and 10 ml of tetrahydrofuran is warmed at 60° C. for 30 min. with stirring. The solvent is evaporated and the residue is dissolved in 10 ml of sodium carbonate solution, and extracted with chloroform (30 ml×3).

The chloroform solution is extracted with 1N-HCl (20ml×3). The aqueous solution is then extracted with chloroform after adding sodium carbonate solution to make basic (pH 10). The solvent is evaporated to give 1.1 g of pale liquid. This liquid is dissolved in 10 ml of dilute HCl solution (pH 5) and stirred for 30 min. The water is evaporate to dryness, and the residue is recrystallized from methanol-ether.

Yield 1.0 g, Colorless Crystals, mp 189.5°–191° C.;
IR(KBr) 3200, 3100, 2700–2500, 1560, 1510, 1310, 1050 cm$^{-1}$;
Anal. Calcd. for $C_{10}H_{18}N_5O_3Cl$: C, 41.17; H, 6.17; N, 24.01 Found: C, 41.04; H, 6.15; N, 24.13

PREPARATION EXAMPLE 15

1-(2'-hydroxy-3'-diethylaminopropyl)-3-nitrotriazole

This compound is obtained in a simmilar manner as preparation example 14, except for the use of diethylamine instead of piperidine. Recrystallization from methanol give colorless crystals. mp 131°–132° C.;
IR(KBr) 3200, 3100, 2700–2500, 1560, 1510, 1310, 1050 cm$^{-1}$;
Anal. Calcd. for $C_9H_{18}N_5O_3Cl$: C, 38.64; H, 6.44; N, 25.04 Found: C, 38.42; H, 6.35; N, 25.21

PREPARATION EXAMPLE 16

1-(2'-hydroxy-3'-N-aziridinopropyl)-3-nitrotriazole

A mixture of 1-(2',3'-epoxypropyl)-3-nitrotriazole (1 g), ethyleneimine (0.5 g) and methanol (10 ml) is refluxed for 2 hr with stirring. The solvent and excess ethyleneimine are removed, and the residue is recrystallized from ethanol-isopropanol to give Colorless crystals (0.72 g). mp 118°–119.5° C.;

IR(KBr) 3400, 3150, 1550, 1360, 1310, 1270, 1120, 1040 cm$^{-1}$;

Anal. Calcd. for $C_7H_{11}N_5O_3$: C, 39.34; H, 5.12; N, 32.87 Found: C, 39.44; H, 5.16; N, 32.86

PREPARATION EXAMPLE 17

2-(4'-nitrotriazolyl) acetic acid methyl ester 4-nitro-1,2,3-triazole (3 g), triethylamine (8 g) and bromoacetic acid methyl ester (6 g) are dissolved in 25 ml of methanol, and then refluxed for 6 hr. Methanol and triethylamine are removed. The residue is poured into water and extracted with chloroform. The extract is dried and evaporated to dryness. Recrystallization from hot benzene give 2-(4'-nitro-1'-triazolyl) acetic acid methyl ester as colorless crystals (1.2 g). mp 110°–111° C.;

IR(KBr) 3120, 1650, 1560, 1550, 1520, 1320, 1300, 1250 cm$^{-1}$;

The filtrate after recrystallization is evaporated to dryness, and the residue is purified by chromatography on silica gel (elution with benzene-ethyl acetate).

2-(4'-nitro-2'-triazolyl) acetic acid methyl ester is obtained as colorless crystals.

Yield 1.3 g, mp 67°–68° C.;

IR(KBr) 3100, 1645, 1540, 1355, 1300, 1235 cm$^{-1}$;

PREPARATION EXAMPLE 18

2-(4'-nitro-1'-triazolyl) acetic acid methoxyethylamide

To a 1 g of 2-(4'-nitro-1'-triazolyl) acetic acid methyl ester in 5 ml of dioxane is added 2 g of methoxyethylamine, and warmed at 100° C. for 1 hr with stirring.

The reactin mixture is evaporated and the residue recrystallized from chloroform. Colorless crystals, mp 122°–123° C.;

IR(KBr) 3350, 3120, 1670, 1560, 1550, 1520, 1310, 1100 cm$^{-1}$;

PREPARATION EXAMPLE 19

2-(4'-nitro-2'-triazolyl) acetic acid methoxyethylamide

This compound is prepared in a similar manner as preparation example 18 except for using 2-(4'-nitro-2'-triazolyl) acetic acid methyl ester instead of 2-(4'-nitro-1'-triazolyl) acetic acid methyl ester.

Colorless crystals, mp 116°–117° C.;

IR(KBr) 3350, 3150, 1670, 1575, 1555, 1355, 1300, 1100 cm$^{-1}$;

PREPARATION EXAMPLE 20

2-(4'-nitro-1'-triazolyl) acetic acid ethanolamide

A mixture of 1 g of 2-(4'-nitro-1'-triazolyl) acetic acid methyl ester. 5 ml of dioxane and 2 g of monoethanolamine is heated at 100° C. for 1 hr with stirring. The reaction mixture is evaporated, and the residue is dissolved in 10 ml of methanol with 3 g of ion exchange resin (Dowex 50W) and stirred for 30 min.

After filtration, the solvent is removed and the residue recrystallized from ethanol-dioxane.

Colorless crystals, mp 129°–130° C.;

IR(KBr) 3470, 3400, 3300, 3120, 3080, 1655, 1560, 1540, 1520, 1320, 1300, 1075, 1100 cm$^{-1}$;

PREPARATION EXAMPLE 21

2-(4'-nitro-2'-triazolyl) acetic acid ethanolamide

This compound is obtained in a similar manner as preparation example 20 except for using 2-(4'-nitro-2'-triazolyl) acetic acid methyl ester.

Colorless crystals, mp 123°–125° C.;

IR(KBr) 3400, 3350, 3150, 1665, 1575, 1560, 1520, 1310, 1210 cm$^{-1}$;

PREPARATION EXAMPLE 22

2-(4'-nitro-1'-triazolyl) acetic acid propanolamide

This compound is obtained in a similar manner as preparation example 20 except for using propanolamine instead of ethanolamine. Colorless crystals, mp 147°–148.5° C.;

IR(KBr) 3400, 3350, 3150, 1670, 1560, 1520, 1310, 1050 cm$^{-1}$;

PREPARATION EXAMPLE 23

1-(2'-hydroxy-3'-chloropropyl)-4-nitro-1,2,3-triazole
and
2-(2'-hydroxy-3'-chloropropyl)-4-nitro-1,2,3-triazole A mixture of 1 g of 4-nitro-1,2,3-triazole, 5 g of epichlorohydrin and 0.2 g of anhyd. potassium carbonate is heated at 100° C. for 1 hr with stirring. The reaction mixture is filtered, and washed with ethanol.

The combined filtrates are evaporated to dryness to give a pale yellow liquid.

This liquid is purified by chromatography on silica gel (elution with $CHCl_3$-isopropylether to give 2-(2'-hydroxy-3'-chloropropyl)-4-nitro-1,2,3-triazole as colorless crystals, mp 73°–74.5° C.;

IR(KBr) 3400, 3150, 1540, 1480, 1390, 1350, 1300, 1040, 830 cm$^{-1}$; and 1-(2'-hydroxy-3'-chloropropyl)-4-nitro-1,2,3-triazole as colorless crystals, mp 83°–84° C.;

IR(KBr) 3400, 3150, 1540, 1510, 1395, 1300, 1040, 830 cm$^{-1}$;

PREPARATION EXAMPLE 24

1-(2',3'-epoxypropyl)-4-nitro-1,2,3-triazole

A mixture of 1 g of 1-(2'-hydroxy-3'-chloropropyl)-4-nitro-1,2,3-triazole and 10 ml of 10% sodium hydroxide solution is stirred for 15 min at room temperature.

The reaction mixture is extracted with chloroform. After drying with anhyd. $MgSO_4$, the solvent is evaporated to dryness. The residue is dissolved in water, and warmed at 60° C. with activated charcoal for 20 min.

After filtration, the filtrate is evaporated under reduced pressure to give 0.7 g of solid.

Colorless crystals, mp 48°–48.5° C.;

IR(KBr) 3150, 1540, 1510, 1480, 1400, 1310, 1260, 1130 cm$^{-1}$;

PREPARATION EXAMPLE 25

2-(2',3'-epoxypropyl)-4-nitro-1,2,3-triazole

This compound is obtained in a similar manner as preparation example 24 except for the use of 2-(2'-hydroxy-3'-chloropropyl)-4-nitro-1,2,3-triazole Colorless crystals, mp 38°–38.5° C.;

IR(KBr) 3150, 1540, 1480, 1390, 1350, 1300, 1260, 1130 cm$^{-1}$;

PRERPARATION EXAMPLE 26

1-(2'-hydroxy-3'-piperidinopropyl)-4-nitro-1,2,3-triazole-hydrochloride

A mixture of 0.5 g of 1-(2'-hydroxy-3'-chloropropyl)-4-nitro-1,2,3-triazole and 3 g of piperidine in 10 ml of THF is refluxed for 1 hr with stirring. The solvent and excess piperidine are removed. The residue is dissolved in chloroform and washed with 5 ml of 1% NaOH solution. The solvent is evaporated to dryness, dissolved in dilute HCl solution washed with chloroform.

A colorless solid is obtained by evaporating the aqueous layer under reduced pressure. Recrystallized from ethanol-isopropanol, mp 140°–141° C.;

IR(KBr) 3250, 2950, 2750, 2650, 1540, 1510, 1480, 1380, 1300, 1110, 1040, 830 $cm^{-1}$;

PREPARATION EXAMPLE 27

1-(2'-hydroxy-3'-methoxypropyl)-4-nitro-1,2,3-triazole
and
2-(2'-hydroxy-3'-methoxypropyl)-4-nitro-1,2,3-triazole A mixture of 1.5 g of 4-nitro-1,2,3-triazole, 7.5 g of methyl glycidyl ether and 0.3 g of anhyd. potassium carbonate is refluxed for 20 min. The reaction mixture is filtered and washed with ethanol.

The combined filtrate is evaporated to get a pale yellow oil. The oil is purified by chromatography on silica gel (elution with chloroform-methanol) to afford 2-(2'-hydroxy-3'-methoxypropyl)-4-nitro-1,2,3-triazole as a colorless solid. mp 58.2°–59° C.;

IR(KBr) 3400, 3150, 1540, 1480, 1450, 1370, 1350, 1300, 1120–1070, 830 $cm^{-1}$;

And 1-(2'-hydroxy-3'-methoxypropyl)-4-nitro-1,2,3-triazole as a pale yellow oil.

IR(neat) 3400, 3150, 1540, 1510, 1480, 1400, 1300, 1130–1080, 830 $cm^{-1}$;

PREPARATION EXAMPLE 28

1-methoxycarbonylmethyl-3-nitor-1,2,4-triazole-5-carboxylic acid methyl ester

To a 1.1 g of 3-nitro-1,2,4-triazole 5-carboxylic acid methyl ester in 10 ml of DMF is added 280 mg of sodium hydride (60% dispersion). Aftre stirring for 20 min. at room temperature, 1.3 g of methyl bromoacetate is added and stirred for 4 hr. at 60°–70° C.

The solvent is removed and the residue extracted with ethyl acetate. Removal of ethyl acetate give 1.1 g of pale yellow oil.

IR(neat) 1740 $cm^{-1}$;

Anal. Calcd for $C_7H_8N_4O_6$: c, 34.40; H, 3.28; N, 23.0 found: C, 34.20; H, 3.26; N, 23.3

PREPARATION EXAMPLE 29

1-(hydroxyethylcarbamoylmethyl)-3-nitro-1,2,4-triazole-5-carboxylic acid ethanolamide To a solution of 530 mg of 1-methoxycarbonylmethyl-3-nitro-1,2,4-triazole-5-carboxylic acid methyl ester is 12 ml of dioxane is added 500 mg of mono-ethanolamine and warmed at 70°–80° C. for 2 hr.

The solvent is removed, and the residue is dissolved in methanol and treated with cation exchange resin (Dowex 50W) to afford a white solid. mp 106°–108° C.;

IR(KBr) 3350, 3300, 1670, 1560, 1530, 1320, 1040, $cm^{-1}$;

Anal. Calcd. for $C_9H_{14}N_6O_6$: C, 35.8; H, 4.64; N, 27.8 Found: C, 36.0; H, 4.65; N, 28.0

PREPARATION EXAMPLE 30

3-nitro-1,2,4-triazole-5-carboxylic acidmethoxyethylamide

To 1 g of 3-nitro-1,2,4-triazole-5-carboxylic acid methyl ester dissolved in 5 ml of dioxane is added 1 g of methoxy ethylamine. The reaction mixture is warmed at 40°–50° C. for 2 hr with stirring.

Removal of solvent and excess amine give a colorless oil.

IR(neat) 3400, 1650, 1540, 1120 $cm^{-1}$;

Anal. Calcd. for $C_6H_9N_5O_4$: C, 33.5; H, 4.19; N, 32.6 Found: C, 33.8; H, 4.20; N, 32.3

PREPARATION EXAMPLE 31

1-methoxycarbonylmethyl-3-nitro-1,2,4-triazole-5-carboxylic acid methoxyethylamide To 1.25 g of 3-nitro-1,2,4-triazole-5-carboxylic acid methoxyethylamide dissolved in 20 ml of DMF is added 280 mg of sodium hydride (60% dispersion).

After stirring for 15 min. at room temperature, 1.3 g of bromo methyl acetate is added and stirred for 2 hr at 60°–70° C.

The solvent is removed and the residue extracted with chloroform. A pale yellow oil is obtained by usual work up.

IR(neat) 3350, 1750, 1690, 1560, 1320, 1230, 1130 $cm^{-1}$;

Anal. Calcd. for $C_9H_{13}N_5O_6$: C, 37.6; H, 4.53; N, 24.4 Found: C, 37.8; H, 4.55; N, 24.7

PREPARATION EXAMPLE 32

1-[N,N-bis(hydroxyethyl)carbamoylmethyl]-3-nitro-1,2,4-triazole-5-carboxylic acid methoxyethylamide To 530 mg of 1-methoxycarbamoylmethyl-3-nitro-1,2,4-triazole-5-carboxylic acid methoxyethylamide dissolved in 3 ml of dioxane is added 1 g of diethanolamine.

The reaction mixture is warmed at 70°–80° C. for 2 hr with stirring. The solvent is removed, and the residue is treated with cation exchange resin (Dowex 50W) and then purified by chromatography on silica gel (elution with chloroform-methanol) to give 300 mg of colorless oil.

IR(neat) 3300–3450, 1650, 1550, 1310, 1120, 1070 $cm^{-1}$;

Anal. Calcd. for $C_{12}H_{20}N_6O_2$: C, 40.0; H, 5.56; N, 23.3 found: C, 40.4; H, 5.48; N, 23.1

PREPARATION EXAMPLE 33

1-methyl-3-nitro-1,2,4-triazole-5-carboxylic acid diethanolamide

To 470 mg of 1-methyl-3-nitro-1,2,4-triazole-5-carboxylic acid methyl ester dissolved in 3 ml of dioxane is added 300 mg of diethanolamine.

The reaction mixture is warmed at 60°–70° C. for 2 hr. After treating with ion exchang resin (Dowex 50W), the solvent is removed and the residue recrystallized from methanol-benzene.

Colorless crystals, mp 111°–113° C.; Ir(KBr) 3300, 1660, 1560, 1310, 1040 $cm^{-1}$;

Anal. Calcd. for $C_8H_{13}N_5O_5$: C, 37.1; H, 5.02; N, 27.0 Found: C, 37.4; H, 5.10; N, 26.8

PREPARATION EXAMPLE 34

1-methyl-3-nitro-1,2,4-triazole-5-carboxylic acid monoethanolamide

This compound is obtained in a similar manner as preparation example 33 except for the use of monoethanolamine instead of diethanolamine. Colorless crystals, mp 108°–111° C.; IR(KBr) 3450, 3250, 1690, 1560, 1310, 1080 cm$^{-1}$;

Anal. Calcd. for $C_6H_{12}N_5O_4$: C, 33.5; H, 4.19; N, 32.6 Found: C, 33.1; H, 4.12; N, 32.9

PREPARATION EXAMPLE 35

1-methyl-3-nitro-1,2,4-triazole-5-carboxylic acid-2,3-dihydroxypropyl amide.

This compound is obtained in a similar manner as preparation example 33 except for the use of 2,3-dihydroxypropylamine.

Colorless solid, mp 125°–126° C.; IR(KBr) 3350, 1690, 1560, 1320, 1040 cm$^{-1}$;

Anal. Calcd. for $C_7H_{11}N_5O_5$: C, 34.3; H, 4.49; N, 28.6 Found: C, 33.8; H, 4.37; N, 28.2

PREPARATION EXAMPLE 36

1-(3'-methoxy-2'-hydroxypropyl)-3-nitro-1,2,4-triazole-5-carboxylic acid methyl ester A mixture of 3-nitro-1,2,4-triazole-5-carboxylic acid methyl ester (2 g), methyl glycidol (6 ml) and anhydrous pottasium carbonate (0.2 g) is warmed at 80° C. for 20 min with stirring.

The reaction mixture is filtered, the filtrate is evaporated to dryness. The residue is purified by column chromatography on silica gel eluted with $CHCl_3$-MeOH to give 1.2 g of colorless oil.

IR(nest) 3400, 1740, 1560, 1310, 1240, 1050 cm$^{-1}$;

Anal. Calcd. for $C_8H_{12}N_4O_6$: C, 36.9; H, 4.62; N, 21.5 Found: C, 36.4; H, 4.75; N, 21.7

PREPARATION EXAMPLE 37

1-(3'-methoxy-2'-hydroxypropyl)-3-nitro-1,2,4-triazole-5-carboxylic acid ethanolamide To a 350 mg of 1-(3'-methoxy-2'-hydroxypropyl)-3-nitro-1,2,4-triazole-5-carboxylic acid methyl ester dissolved in 5 ml of dioxane is added 500 mg of monoethanolamine. The mixture is warmed at 100° C. for 3 hr with stirring. the reaction mixture is treated with cation exchange resin (Dowex 50W), and the resin is filtered off.

The filtrate is evaporated, and the residue is purified by chromatography on silica gel eluted with chloroform-methanol to give 0.3 g of colorless oil.

IR(neat) 3300-3400, 1675, 1555, 1310, 1120, 1060 cm$^{-1}$;

Anal. Calcd. for $C_9H_{15}N_5O_6$: C, 37.4; H, 5.19; N, 24.2 found: C, 37.1; H, 5.12; N, 23.9

PREPARATION EXAMPLE 38

1-(3'-methoxy-2'-hydroxypropyl)-3-nitro-1,2,4-triazole-5-carboxylic acid diethanolamide This compound is obtained in a similar manner as preparation example 37 except for the use of diethanolamine instead of monoethanolamine. Colorless oil;

IR(neat) 3250-3400, 1670, 1555, 1320, 1120, 1055 cm$^{-1}$;

Anal. Calcd. for $C_{11}H_{19}N_5O_7$: C, 39.6; H, 5.71; N, 21.0 Found: C, 39.8; H, 55.8; N, 20.7

PREPARATION EXAMPLE 39

1-(2'-hydroxyethyl)-3-nitro-1,2,4-triazole-5-carboxylic acid ethanolamide a mixture of 3-nitro-1,2,4-triazole-5-carboxylic acid methyl ester (3.0 g), ethylene oxide (1.53 g) and sodium methoxide (0.1 g) is dissolved in 6 ml of methanol, and warmed at 50°–55° C. for 1.5 hr with stirring. The solvent is removed to get 1.94 g of colorless solid. The solid is dissolved in 10 ml of dioxane and then 0.62 g of monoethanolamine is added.

The mixture is warmed at 80°–100° C. for 3 hr with stirring. The solvent is removed, and the residue is treated with cation exchange resin (Dowex 50W) and then purified by chromatography on silica gel to get colorless solid (elution with chloroform-MeOH). mp. 108°–110° C.;

IR(KBr) 3400, 3250, 1670, 1555, 1320, 1060 cm$^{-1}$;

Anal. Calcd. for $C_7H_{11}N_5O_5$: C, 34.3; H, 4.49; N, 28.6 Found: C, 34.0; H, 4.45; N, 28.8

The dose of each compound of the present invention as described above, which serves as a useful sensitizer in radiotherapy, varies depending on the tumor to be treated and the type of the compound per se. Generally preferable doses thereof are 20 to 10000 mg, 0.5 to 10000 mg and 20 to 10000 mg in the cases of an oral preparation, an injection and a suppository, respectively. The optimum dose is to be determined by a physician depending on various factors including the symptom, the type of radiation, the exposure dose and the extent of divisional irradiation.

The way for the administration of the compound of the present invention is not particularly restricted. Thus it may be formulated in a preparation together with carriers conventionally employed in the art in a conventional manner.

To further illustrate the effect of the compound of the present invention as a radiation sensitizer, the following Examples will be given.

EXAMPLE 1

In order to examine a radiation sensitizing effect on V-79 Chinese hamster cells, 100,000 said cells were cultured in a single layer within a petri dish to thereby prepare V-79 cells in the logatithmic phase.

A medium solution of a sample compound at a given concentration was added to the petri dish and allowed to stand at 37° C. for 60 min. Then the petri dish was placed in a sealed container at room temperature and nitrogen gas was passed therethrough for 10 min to thereby remove oxygen. Subsequently the cells were irradiated with X-ray in a dose of 1.6 Gy/min.

After the irradiation, the cells were washed with a phosphate buffer solution and treated with trypsin to give single cells. A given amount of the single cells were introduced into a culture dish and 5 ml of a medium was added thereto. After culturing at 37° C. for seven days, the cells were stained and washed with water. Then the colonies thus formed were counted.

For comparison, the procedure as described above was repeated except that a medium solution containing no sample compound was irradiated either under a nitrogen stream or in the presence of air.

The logarithm of the survival ratio of the cells calculated from the obtained data was plotted against the exposure dose to give a linear relationship.

Then the induction period dose D, (Gy) was determined from the point at which the straight line crossed with a horizontal line showing a survival ratio of 1.0. On the other hand, the exposure dose required to lower the survival ratio to 1/10 $D_{10}$ (Gy) was determined from the slope of the abovementioned line.

Further the exposure dose required for inactivating 99.9% of cells ($D_{0.1\%} = D_4 + 3D_{10}$) was determined. The ratios of the $D_{0.1\%}$ to that obtained by irradiating in the air ($D_{0.1\%}/D_{0.1\%}$) and to that obtained by irradiating under a nitrogen stream ($D_{0.1\%}/D_{0.1\%}$) were determined and respectively defined as the sensitizing ratio on the basis of air (SARA) and the sensitizing ratio on the basis of nitrogen (SARA on $N_2$ basis).

Table 1 shows the result.

EXAMPLE 2

$10^5$ EMT-6 tumor cells were subcutaneously inoculated into the both thighs of a male Balb/C mouse aged eight weeks. Each group had four animals. When the diameter of a tumor induced by the inoculated tumor cells reached approximately 1 cm. 200 mg/kg of a solution of a sample compound in a physiological saline solution was intraperitonearlly administered to the animal. After 40 min, the animal was irradiated with X-ray in a dose of 450 rad/min and killed five min after the irradiation.

The killed animal was systemically sterilized with 70% ethanol and the tumor region was taken out. The tissue was cut into pieces and mixed with 22 ml of trypsin. The obtained mixture was stirred at 37° C. for 50 min. Then the supernatant was collected and cells contained therein were counted. A given amount of the cells were placed on a plastic plate of 5 cm in diameter and 5 ml of a medium was added thereto. Then the cells were cultured in a $CO_2$ incubator. Cells not irradiated with X-ray were taken out from the incubator after nine days while those irradiated with X-ray were taken out therefrom after ten days. These cells were fixed with methanol and stained with a Giemsa solution. Then the colonies thus formed were counted.

The survival ratio was determined with the use of the unirradiated cells as a control. Table 2 shows the result.

EXAMPLE 3

In order to examine the radiation sensitizing effect on V-79 Chinese hamster cells, 100,000 said cells were cultured in a single layer within a petri dish to thereby give V-79 cells in the logarithmic phase.

A medium solution of a sample compound at a given concentration was added to the petri dish and allowed to stand at 37° C. for 60 min. Then the petri dish was introduced into a sealed container at room temperature and nitrogen gas was passed therethrough for 10 min to thereby remove oxygen. Then the cells were irradiated with X-ray in a dose of 1.6 Gy/min.

After the irradiation, the cells were washed with a phosphate buffer solution and treated with trypsin to give single cells. A given amount of the single cells were introduced into a culture dish and 5 ml of a medium was added thereto. After culturing at 37° C. for seven days, the cells were stained and washed with water. Then the colonies thus formed were counted.

For comparison, the procedure as described above was repeated except that a medium solution containing no sample compound was irradiated either under a nitrogen stream or in the presence of air.

The logarithm of the survival ratio of the cells calculated from the obtained data was plotted against the exposure dose to give a linear relationship.

The induction period dose $D_q$ (Gy) was determined from the point at which the above straight line crossed with a horizontal line showing a survival ratio of 1.0. On the other hand, the exposure dose required for lowering the survival ratio to 1/10 $D_{10}$ (Gy) was determined from the slope of the above straight line.

Further the exposure dose required for inactivating 99.9% of the cells ($D_{0.1\%} = D_q + D_{10}$) was determined. The ratios of the $D_{0.1\%}$ to that obtained by irradiating in the air ($D_{0.1\%}^{air}/D_{0.1\%}$) and to that obtained by irradiating under a nitrogen stream ($D_{0.1\%}^{N_2}/D_{0.1\%}$) were determined and respectively defined as the sensitizing ratio on the basis of air (SARA) and the sensitizing ratio on the basis of nitrogen (SARA on $N_2$ basis).

Table 3 shows the result.

EXAMPLE 4

$10^5$ EMT-6 tumor cells were subcutaneously inoculated to the both thighs of a male Balb/C mouse aged eight weeks. Each group had four animals. When the diameter of a tumor induced by the inoculated tumor cells reached approximately 1 cm. 200 mg/kg of a solution of a sample compound in a physiological saline solution was intraperitoneally administered to the animal. 40 min after the administration, the mouse was irradiated with X-ray in a dose of 450 rad/min and killed five min after the irradiation.

The killed animal was systemically sterilized with 70% ethanol and the tumor region was taken out. The tissue was cut into pieces and mixed with 22 ml of trypsin. The obtained mixture was stirred at 37° C. for 50 min. Then the supernatant was collected and cells contained therein were counted. A given amount of the cells were placed on a plastic plate of 5 cm in diameter and 5 ml of a medium was added thereto. Then the cells were cultured in a $CO_2$ incubator. Cells not irradiated with X-ray were taken out from the incubator after nine days while those irradiated with X-ray were taken out therefrom after ten days. These cells were fixed with methanol and stained with a Giemsa solution. Then the colonies thus formed were counted.

The survival ratio was determined with the use of the unirradiated cells as a control. Table 4 shows the result.

EXAMPLE 5

In order to examine the radiation sensitizing effect on V-79 Chinese hamster cells, 100,000 said cells were cultured in a single layer within a petri dish to thereby prepare V-79 cells in the logarithmic phase.

A medium solution of a sample compound at a given concentration was added to the petri dish and allowed to stand at 37° C. for 60 min. Then the petri dish was introduced into a sealed container at room temperature and nitrogen gas was passed therethrough for 10 min to thereby remove oxygen. Then the cells were irradiated with X-ray in a dose of 1.6 Gy/min.

After the irradiation, the cells were washed with a phosphate buffer solution and treated with trypsin to give single cells. Then a given amount of the single cells were introduced into a culture dish and 5 ml of a medium was added thereto. After culturing at 37° C. for seven days, the cells were stained and washed with water. Then the colonies thus formed were counted.

For comparison, the procedure as described above was repeated except that a medium solution containing no sample compound was irradiated either under a nitrogen stream or in the presence of air.

The logarithm of the survival ratio culculated from the obtained data was plotted against the exposure dose to give a linear relationship.

The induction period dose $D_q(Gy)$ was determined from the point at which this straight line crossed with a horizontal line showing a survival ratio of 1.0. On the other hand, the exposure dose required for lowering the survival ratio to 1/10 $D_{10}$ (Gy) was determined from the slope of the above straight chain.

Further the exposure dose required for inactivating 99.9% of the cells ($D_{0.1\%}=D_q+3D_{10}$) was determined. Ratios of the $D_{0.1\%}$ to that obtained by irradiating in the air ($D_{0.1\%}^{air}/D_{0.1\%}$) and that obtained by irradiating under a nitrogen stream ($D_{0.1\%}^{N_2}/D_{0.1\%}$) were determined and respectively defined as the sensitizing ratio on the basis of air (SARA) and the sensitizing ratio on the basis of nitrogen (SARA on $N_2$ basis).

Table 5 shows the result.

EXAMPLE 6

10 EMT-6 tumor cells were subcutaneously inoculated to the both thighs of a male Balb/C mouse aged eight weeks. Each group had four animals. When the diameter of a tumor induced by the inoculated tumor cells reached approximately 1 cm. 200 mg/kg of a solution of a sample compound in a physiological saline solution was intraperitoneally administered. After 40 min. the animal was irradiated with X-ray in a dose of 450 rad/min and killed five min after the irradiation.

The killed animal was systemically sterilized with 70% ethanol and the tumor region was taken out. The tissue was cut into pieces and mixed with 22 ml of trypsin. The mixture was stirred at 37° C. for 50 min. Then the supernatant was collected and cells contained therein were counted. A given amount of the cells were placed on a plastic plate of 5 cm in diameter and 5 ml of a medium was added thereto. The cells were cultured in a $CO_2$ incubator. Cells not irradiated with X-ray were taken out from the incubator after nine days while those irradiated with X-ray were taken out therefrom after ten days. These cells were fixed with methanol and stained with A Giemsa solution. Then the colonies thus formed were counted.

The survival ratio was determined with the use of the unirradiated cells as a control. Table 6 shows the result.

TABLE 1

| No | Sample compound | Concentration (m mole) | $D_q$ (Gy) | $D_{10}$ (Gy) | $D_{0.1\%}$ (Gy) | SARA | SARA on $N_2$ basis |
|---|---|---|---|---|---|---|---|
| Control | | | | | | | |
| 1-1 | None (in the air) | — | 2.4 | 3.5 | 12.9 | 1.00 | 2.40 |
| 1-2 | None (under nitrogen stream) | — | 5.8 | 8.4 | 31.0 | 0.42 | 1.00 |
| Example | | | | | | | |
| 1-1 | 2-(3'-Nitro-1'-triazolyl)acetic acid methyl ester | 2.0 | 3.3 | 4.7 | 17.4 | 0.74 | 1.78 |
| 1-2 | 2-(3'-Nitro-1'-triazolyl)acetic acid hydroxyethyl ester | 2.0 | 3.3 | 4.6 | 17.1 | 0.75 | 1.81 |
| 1-3 | 2-(3'-Nitro-1'-triazolyl)acetic acid ethoxyethyl ester | 2.0 | 3.2 | 4.7 | 17.3 | 0.75 | 1.79 |
| 1-4 | 2-(3'-Nitro-1'-triazolyl)acetic acid morpholide | 2.0 | 2.6 | 3.9 | 14.3 | 0.90 | 2.17 |
| 1-5 | 2-(3'-Nitro-1'-triazolyl)acetic acid morpholide | 5.0 | 2.3 | 3.6 | 13.1 | 0.98 | 2.37 |
| 1-6 | 2-(3'-Nitro-1'-triazolyl)acetic acid piperidide | 2.0 | 2.9 | 4.6 | 16.7 | 0.77 | 1.86 |
| 1-7 | 2-(3'-Nitro-1'-triazolyl)acetic acid amide | 2.0 | 3.2 | 4.7 | 17.3 | 0.75 | 1.79 |
| 1-8 | 2-(3'-Nitro-1'-triazolyl)acetic acid ethanolamide | 2.0 | 2.8 | 4.1 | 15.1 | 0.85 | 2.05 |
| 1-9 | 2-(3'-Nitro-1'-triazolyl)acetic acid butylamide | 2.0 | 3.3 | 4.8 | 17.7 | 0.73 | 1.75 |
| 1-10 | 2-(3'-Nitro-1'-triazolyl)acetic acid 2''-methoxyethylamide | 2.0 | 2.9 | 4.6 | 16.7 | 0.77 | 1.86 |
| 1-11 | 2-(3'-Nitro-1'-triazolyl)acetic acid 4''-methylpiperazide | 2.0 | 2.8 | 4.2 | 15.4 | 0.84 | 2.01 |
| 1-12 | 2-(3'-Nitro-1'-triazolyl)acetic acid 3''-dimethylaminopropylamide | 2.0 | 2.8 | 4.5 | 16.3 | 0.79 | 1.90 |
| 1-13 | 2-(3'-Nitro-1'-triazolyl)propionic acid methyl ester | 2.0 | 3.4 | 4.9 | 18.1 | 0.71 | 1.71 |
| 1-14 | 2-(3'-Nitro-1'-triazolyl)propionic acid 2''-piperidinoethylamide | 2.0 | 3.2 | 4.6 | 17.0 | 0.76 | 1.82 |
| 1-15 | 2-(3'-Nitro-1'-triazolyl)propionic acid ethanolamide | 2.0 | 3.0 | 4.3 | 15.9 | 0.81 | 1.95 |
| 1-16 | 2-(3'-Nitro-1'-triazolyl)propionic acid morpholide | 2.0 | 3.0 | 4.1 | 15.3 | 0.84 | 2.03 |
| 1-17 | 1-(2'-Hydroxy-3'-chloropropyl)-3-nitrotriazole | 2.0 | 3.4 | 5.0 | 18.4 | 0.70 | 1.68 |
| 1-18 | 1-(2',3'-Epoxypropyl)-3-nitro-triazole | 2.0 | 3.4 | 4.9 | 18.1 | 0.71 | 1.71 |
| 1-19 | 1-(2'-Hydroxy-3'-methoxypropyl)-3-nitrotriazole | 2.0 | 3.1 | 4.4 | 16.3 | 0.79 | 1.90 |
| 1-20 | 1-(2'-Hydroxy-3'-chloropropyl)-3-nitrotriazole | 2.0 | 3.0 | 4.1 | 15.3 | 0.84 | 2.03 |
| 1-21 | 1-(2'-Hydroxy-3'-ethoxypropyl)-3-nitrotriazole | 2.0 | 3.1 | 4.4 | 16.3 | 0.79 | 1.90 |
| 1-22 | 1-(2'-Hydroxy-3'-piperidinopropyl)-3-nitrotriazole hydrochloride | 2.0 | 3.0 | 4.3 | 15.9 | 0.81 | 1.95 |
| 1-23 | 1-(2'-Hydroxy-3'-diethylamino- | 2.0 | 3.0 | 4.3 | 15.9 | 0.81 | 1.95 |

TABLE 1-continued

| No | Sample compound | Concentration (m mole) | $D_q$ (Gy) | $D_{10}$ (Gy) | $D_{0.1\%}$ (Gy) | SARA | SARA on $N_2$ basis |
|---|---|---|---|---|---|---|---|
| | propyl)-3-nitrotriazole hydrochloride | | | | | | |
| 1-24 | 1-(2'-Hydroxy-3'-acetoxypropyl)-3-nitrotriazole | 2.0 | 3.2 | 4.6 | 17.0 | 0.76 | 1.82 |
| 1-25 | 1-(2'-Hydroxyethyl)-3-nitrotriazole | 2.0 | 3.4 | 4.8 | 17.8 | 0.72 | 1.74 |
| 1-26 | 1-(2'-Acetoxyethyl)-3-nitrotriazole | 2.0 | 3.4 | 4.8 | 17.8 | 0.72 | 1.74 |
| 1-27 | 1-(3'-Nitro-1'-triazolyl)glucose | 2.0 | 3.1 | 4.3 | 16.0 | 0.81 | 1.94 |
| 1-28 | 1-(2'-Hydroxyethyl-3'-aziridinopropyl)-3-nitrotriazole | 2.0 | 2.5 | 3.9 | 14.2 | 0.91 | 2.18 |

TABLE 2

| No | Sample compound | Irradiation dose (Gy) | Amount of cells per plate | Amount of colonies | Survival ratio (%) |
|---|---|---|---|---|---|
| Control | | | | | |
| 2-1 | None | 0 | 100 | 58 | — |
| 2-2 | None | 20 | 5000 | 26 | 0.90 |
| Example | | | | | |
| 2-1 | 2-(3'-Nitro-1'-triazolyl)acetic acid methyl ester | 20 | 30000 | 52 | 0.30 |
| 2-2 | 2-(3'-Nitro-1'-triazolyl)acetic acid morpholide | 20 | 30000 | 13 | 0.07 |
| 2-3 | 2-(3'-Nitro-1'-triazolyl)acetic acid ethanolamide | 20 | 30000 | 16 | 0.09 |
| 2-4 | 2-(3'-Nitro-1'-triazolyl)propionic acid morpholide | 20 | 30000 | 18 | 0.10 |
| 2-5 | 1-(2'-Hydroxy-3'-methoxypropyl)-3-nitrotriazole | 20 | 30000 | 18 | 0.10 |
| 2-6 | 1-(2'-Hydroxyethyl)-3-nitrotriazole | 20 | 30000 | 25 | 0.14 |
| 2-7 | 1-(3'-Nitro-1'triazolyl)ribose | 20 | 30000 | 28 | 0.16 |
| 2-8 | 1-(2'-Hydroxyethyl-3'-aziridinopropyl)-3-nitrotriazole | 20 | 30000 | 11 | 0.06 |

TABLE 3

| No | Sample compound | Concentration (m mole) | $D_q$ (Gy) | $D_{10}$ (Gy) | $D_{0.1\%}$ (Gy) | SARA | SARA on $N_2$ basis |
|---|---|---|---|---|---|---|---|
| Control | | | | | | | |
| 3-1 | None (in the air) | — | 2.8 | 4.1 | 15.1 | 1.00 | 2.25 |
| 3-2 | None (under nitrogen stream) | — | 6.4 | 9.2 | 34.0 | 0.44 | 1.00 |
| Example | | | | | | | |
| 3-1 | 2-(4'-Nitro-1'-triazolyl)acetic acid methyl ester | 2.0 | 4.1 | 5.8 | 21.5 | 0.70 | 1.58 |
| 3-2 | 2-(4'-Nitro-1'-triazolyl)acetic acid methyl ester | 10.0 | 3.9 | 5.4 | 20.1 | 0.75 | 1.69 |
| 3-3 | 2-(4'-Nitro-2'-triazolyl)acetic acid methyl ester | 2.0 | 3.7 | 5.1 | 19.0 | 0.79 | 1.79 |
| 3-4 | 2-(4'-Nitro-1'-triazolyl)acetic acid methoxyethylamide | 2.0 | 5.2 | 5.7 | 22.3 | 0.68 | 1.52 |
| 3-5 | 2-(4'-Nitro-1'-triazolyl)acetic acid methoxyethylamide | 10.0 | 4.9 | 5.3 | 20.8 | 0.73 | 1.63 |
| 3-6 | 2-(4'-Nitro-2'-triazolyl)acetic acid methoxyethylamide | 2.0 | 4.5 | 6.4 | 23.7 | 0.64 | 1.43 |
| 3-7 | 2-(4'-Nitro-2'-triazolyl)acetic acid methoxyethylamide | 5.0 | 4.3 | 6.2 | 22.9 | 0.69 | 1.48 |
| 3-8 | 2-(4'-Nitro-1'-triazolyl)acetic acid ethanolamide | 2.0 | 4.3 | 5.9 | 22.0 | 0.69 | 1.55 |
| 3-9 | 2-(4'-Nitro-1'-triazolyl)acetic acid ethanolamide | 10.0 | 4.0 | 5.7 | 21.2 | 0.71 | 1.60 |
| 3-10 | 2-(4'-Nitro-2'-triazolyl)acetic acid ethanolamide | 2.0 | 4.5 | 5.8 | 21.9 | 0.69 | 1.55 |
| 3-11 | 2-(4'-Nitro-1'-triazolyl)acetic acid propanolamide | 2.0 | 4.4 | 6.1 | 22.7 | 0.67 | 1.50 |
| 3-12 | 1-(2'-Hydroxy-3'-chloropropyl)-4-nitro-1,2,3-triazole | 2.0 | 4.4 | 6.0 | 22.4 | 0.67 | 1.52 |
| 3-13 | 2-(2'-Hydroxy-3'-chloropropyl)-4-nitro-1,2,3-triazole | 2.0 | 4.5 | 6.1 | 22.8 | 0.66 | 1.49 |
| 3-14 | 1-(2',3'-Epoxypropyl)-4-nitro-1,2,3-triazole | 2.0 | 4.5 | 6.3 | 23.4 | 0.65 | 1.45 |
| 3-15 | 2-(2',3'-Epoxypropyl)-4-nitro-1,2,3-triazole | 2.0 | 4.5 | 6.3 | 23.4 | 0.65 | 1.45 |
| 3-16 | 1-(2'-Hydroxy-3'-piperidinopropyl)-4-nitro-1,2,3-triazole | 2.0 | 4.4 | 5.9 | 22.1 | 0.68 | 1.54 |
| 3-17 | 1-(2'-Hydroxy-3'-methoxypropyl)-4-nitro-1,2,3-triazole | 2.0 | 4.5 | 6.6 | 24.3 | 0.62 | 1.40 |

TABLE 3-continued

| No | Sample compound | Concentration (m mole) | $D_q$ (Gy) | $D_{10}$ (Gy) | $D_{0.1\%}$ (Gy) | SARA | SARA on $N_2$ basis |
|---|---|---|---|---|---|---|---|
| 3-18 | 2-(2'-Hydroxy-3'-methoxypropyl)-4-nitro-1,2,3-triazole | 2.0 | 4.5 | 6.6 | 24.3 | 0.62 | 1.40 |
| 3-19 | 1-(2'-Hydroxy-3'-aziridinopropyl)-4-nitro-1,2,3-triazole | 2.0 | 4.2 | 5.6 | 21.0 | 0.72 | 1.62 |
| 3-20 | 2-(2'-Hydroxy-3'-aziridinopropyl)-4-nitro-1,2,3-triazole | 2.0 | 4.2 | 5.5 | 20.7 | 0.73 | 1.64 |
| 3-21 | 2-(4'-Nitro-1'-triazolyl)ribofranose | 2.0 | 4.6 | 6.7 | 24.7 | 0.61 | 1.38 |
| 3-22 | 2-(4'-Nitro-2'-triazolyl)ribofranose | 2.0 | 4.5 | 6.7 | 24.6 | 0.61 | 1.38 |

TABLE 4

| No | Sample compound | Irradiation dose (Gy) | Amount of cells per plate | Amount of colonies | Survival ratio (%) |
|---|---|---|---|---|---|
| Control | | | | | |
| 4-1 | None | 0 | 100 | 58 | — |
| 4-2 | None | 20 | 5000 | 26 | 0.90 |
| Example | | | | | |
| 4-1 | 2-(4'-Nitro-1'-triazolyl)acetic acid methoxyethylamide | 20 | 30000 | 23 | 0.13 |
| 4-2 | 2-(3'-Nitro-2'-triazolyl)acetic acid methoxyethylamide | 20 | 30000 | 24 | 0.14 |
| 4-3 | 2-(4'-Nitro-1'-triazolyl)acetic acid ethanolamide | 20 | 30000 | 25 | 0.14 |
| 4-4 | 1-(2'-Hydroxy-3'-chloropropyl)-4-nitro-1,2,3-triazole | 20 | 30000 | 8 | 0.05 |
| 4-5 | 2-(2'-Hydroxy-3'-chloropropyl)-4-nitro-1,2,3-triazole | 20 | 30000 | 9 | 0.05 |
| 4-6 | 2-(2',3'-Epoxypropyl)-4-nitro-1,2,3-triazole | 20 | 30000 | 26 | 0.15 |
| 4-7 | 1-(2'-Hydroxy-3'-piperidinopropyl)-4-nitro-1,2,3-triazole | 20 | 30000 | 23 | 0.13 |
| 4-8 | 1-(2'-Hydroxy-3'-methoxypropyl)-4-nitro-1,2,3-triazole | 20 | 30000 | 28 | 0.16 |

TABLE 5

| No | Sample compound | Concentration (m mole) | $D_q$ (Gy) | $D_{10}$ (Gy) | $D_{0.1\%}$ (Gy) | SARA | SARA on $N_2$ basis |
|---|---|---|---|---|---|---|---|
| Control | | | | | | | |
| 5-1 | None (in the air) | — | 2.4 | 3.5 | 12.9 | 1.00 | 2.40 |
| 5-2 | None (under nitrogen stream) | — | 5.8 | 8.4 | 31.0 | 0.42 | 1.00 |
| 5-3 | 1-(3'-Methoxy-2'-hydroxypropyl)-2-nitroimidazole | 1.0 | 3.9 | 6.1 | 22.2 | 0.58 | 1.40 |
| Example | | | | | | | |
| 5-1 | 1-Methoxycarbonylmethyl-3-nitro-1,2,4-triazole-5-carboxylic acid methyl ester | 1.0 | 3.8 | 5.6 | 20.6 | 0.63 | 1.50 |
| 5-2 | 1-(Hydroxyethoxyethylcarbonylmethyl)-3-nitro-1,2,4-triazole-5-carboxylic acid hydroxyethoxyethyl ester | 1.0 | 3.8 | 5.5 | 20.3 | 0.64 | 1.53 |
| 5-3 | 1-(Hydroxyethylcarbamoylmethyl)-3-nitro-1,2,4-triazole-5-carboxylic acid ethanolamide | 1.0 | 3.4 | 4.9 | 18.1 | 0.71 | 1.71 |
| 5-4 | 1-(Morpholinocarbonylmethyl)-3-nitro-1,2,4-triazole-5-carboxylic acid morpholide | 1.0 | 3.3 | 5.0 | 18.3 | 0.70 | 1.69 |
| 5-5 | 1-Dimethylaminopropylcarbamoylmethyl-3-nitro-1,2,4-triazole-5-carboxylic acid dimethylaminopropylamide | 1.0 | 3.3 | 4.8 | 17.7 | 0.73 | 1.75 |
| 5-6 | 1-(4'-Methylpiperazinocarbonylmethyl)-3-nitro-1,2,4-triazole-5-carboxylic acid (4''-methylpiperazide) | 1.0 | 3.4 | 4.9 | 18.1 | 0.71 | 1.71 |
| 5-7 | 3-Nitro-1,2,4-triazole-5-carboxylic acid methoxyethylamide | 1.0 | 3.7 | 5.5 | 20.2 | 0.64 | 1.53 |
| 5-8 | 1-Methoxycarbonylmethyl-3-nitro-1,2,4-triazole-5-carboxylic acid methoxyethylamide | 1.0 | 3.7 | 5.3 | 19.6 | 0.66 | 1.58 |
| 5-9 | 1-(N,N—Bis(2'-hydroxyethyl)-carbamoylmethyl)-3-nitro-1,2,4-triazole-5-carboxylic acid methoxyethylamide | 1.0 | 3.2 | 4.6 | 17.0 | 0.76 | 1.82 |
| 5-10 | 1-Methyl-3-nitro-1,2,4-triazole- | 1.0 | 3.6 | 4.9 | 18.3 | 0.70 | 1.69 |

TABLE 5-continued

| No | Sample compound | Concentration (m mole) | Dq (Gy) | D$_{10}$ (Gy) | D$_{0.1\%}$ (Gy) | SARA | SARA on N$_2$ basis |
|---|---|---|---|---|---|---|---|
| | 5-carboxylic acid diethanolamide | | | | | | |
| 5-11 | 1-Methyl-3-nitro-1,2,4-triazole-5-carboxylic acid monoethanolamide | 1.0 | 3.6 | 5.0 | 18.6 | 0.69 | 1.67 |
| 5-12 | 1-Methyl-3-nitro-1,2,4-triazole-5-carboxylic acid 2',3'-dihydroxypropylamide | 1.0 | 3.7 | 5.1 | 19.0 | 0.68 | 1.63 |
| 5-13 | 1-(2',3'-Epoxypropyl)-3-nitro-1,2,4-triazole-5-carboxylic acid ethanolamide | 1.0 | 3.8 | 5.0 | 18.8 | 0.69 | 1.65 |
| 5-14 | 1-(3'-Methoxy-2'-hydroxypropyl)-3-nitro-1,2,4-triazole-5-carboxylic acid methyl ester | 1.0 | 3.8 | 5.3 | 19.7 | 0.65 | 1.57 |
| 5-15 | 1-(3'-Methoxy-2'-hydroxypropyl)-3-nitro-1,2,4-triazole-5-carboxylic acid ethanolamide | 1.0 | 3.5 | 5.2 | 19.1 | 0.68 | 1.62 |
| 5-16 | 1-(3'-Methoxy-2'-hydroxypropyl)-3-nitro-1,2,4-triazole-5-carboxylic acid diethanolamide | 1.0 | 3.4 | 5.0 | 18.4 | 0.70 | 1.68 |
| 5-17 | 1-(2'-Hydroxyethyl)-3-nitro-1,2,4-triazole-5-carboxylic acid ethanolamide | 1.0 | 3.6 | 5.1 | 18.9 | 0.68 | 1.64 |
| 5-18 | 1-(3'-Aziridino-2'-hydroxypropyl)-3-nitro-1,2,4-triazole-5-carboxylic acid methyl ester | 0.2 | 3.7 | 5.4 | 19.9 | 0.65 | 1.56 |
| 5-19 | 1-(3'-Nitro-5'-bromo-1',2',4'-triazol-1'-yl)acetic acid ethanolamide | 1.0 | 3.7 | 5.5 | 20.2 | 0.64 | 1.53 |
| 5-20 | 1-(3'-Nitro-5'-bromo-1',2',4'-triazol-1'-yl)acetic acid diethanolamide | 1.0 | 3.6 | 5.4 | 19.8 | 0.65 | 1.57 |
| 5-21 | 1-(3'-Nitro-5'-bromo-1',2',4'-triazol-1'-yl)acetic acid methoxyethylamide | 1.0 | 3.7 | 5.4 | 19.9 | 0.65 | 1.56 |
| 5-22 | 1-(3'-Methoxy-2'-hydroxypropyl)-3-nitro-5-bromo-1,2,4-triazole | 1.0 | 3.5 | 5.3 | 19.4 | 0.66 | 1.60 |

TABLE 6

| No | Sample compound | Irradiation dose (Gy) | Amount of cells per plate | Amount of colonies | Survival ratio (%) |
|---|---|---|---|---|---|
| Control | | | | | |
| 6-1 | None | 0 | 100 | 58 | — |
| 6-2 | None | 20 | 5000 | 26 | 0.90 |
| 6-3 | 1-(3'-Methoxy-2'-hydroxypropyl)-2-nitroimidazole | 20 | 30000 | 28 | 0.16 |
| Example | | | | | |
| 6-1 | 1-(Hydroxyethylcarbamoylmethyl)-3-nitro-1,2,4-triazole-5-carboxylic acid ethanolamide | 20 | 30000 | 23 | 0.13 |
| 6-2 | 3-Nitro-1,2,4-triazole-5-carboxylic acid methoxyethylamide | 20 | 30000 | 24 | 0.14 |
| 6-3 | 1-(N,N—Bis(hydroxyethyl)carbamoylmethyl)-3-nitro-1,2,4-triazole-5-carboxylic acid methoxyethylamide | 20 | 30000 | 25 | 0.14 |
| 6-4 | 1-Methyl-3-nitro-1,2,4-triazole-5-carboxylic acid diethanolamide | 20 | 30000 | 8 | 0.05 |
| 6-5 | 1-Methyl-3-nitro-1,2,4-triazole-5-carboxylic acid monoethanolamide | 20 | 30000 | 9 | 0.05 |
| 6-6 | 1-Methyl-3-nitro-1,2,4-triazole 5-carboxylic acid 2',3'-dihydroxypropylamide | 20 | 30000 | 26 | 0.15 |
| 6-7 | 1-(3'-Methoxy-2'-hydroxypropyl)-3-nitro-1,2,4-triazole-5-carboxylic acid ethanolamide | 20 | 30000 | 23 | 0.13 |
| 6-8 | 1-(3'-Methoxy-2'-hydroxypropyl)-3-nitro-1,2,4-triazole-5-carboxylic acid diethanolamide | 20 | 30000 | 23 | 0.16 |
| 6-9 | 1-(3'-Aziridino-2'-hydroxypropyl)-3-nitro-1,2,4-triazole-5-carboxylic acid diethanolamide[*1] | 20 | 30000 | 28 | 0.16 |
| 6-10 | 1-(2'-Hydroxyethyl)-3-nitro-1,2,4-triazole-5-carboxylic acid ethanolamide | 20 | 30000 | 26 | 0.15 |

[*1] added amount is 80 mg

What is claimed is:

1. A radiation sensitizer containing a nitrotriazole compound represented by following formula (I) as an active ingredient:
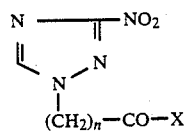
(I)
wherein, n is one or two, X is —NH—R$_1$—OH R$_1$ is alkylene group having two or three carbon atoms.
2. The radiation sensitizer of claim 1, wherein the compound of formula (I) is 2-(3'-nitro-1'-triazolyl)acetic acid ethanol amide.
* * * * *